United States Patent [19]

Quenin et al.

[11] Patent Number: 5,059,393
[45] Date of Patent: Oct. 22, 1991

[54] ANALYSIS SLIDE POSITIONING APPARATUS AND METHOD FOR A CHEMICAL ANALYZER

[75] Inventors: John A. Quenin, Rochester; Johannes J. Porte, Webster; Raymond F. Jakubowicz, Rush, all of N.Y.

[73] Assignee: Eastman Kodak Company, Rochester, N.Y.

[21] Appl. No.: 293,717

[22] Filed: Jan. 5, 1989

[51] Int. Cl.$^5$ .............. G01N 35/00; G01N 35/04; F16H 25/12; F16H 25/16

[52] U.S. Cl. .............................. 422/64; 422/63; 422/67; 422/99; 422/100; 436/46; 436/50; 74/54; 74/55; 74/57

[58] Field of Search ............... 422/50, 63, 64, 65, 422/67, 99, 100, 102; 436/45, 46, 48, 50; 74/567, 568 R, 568 M, 569, 53, 54, 55, 56, 57

[56] References Cited

U.S. PATENT DOCUMENTS

| | | | |
|---|---|---|---|
| 4,041,995 | 8/1977 | Columbus | 141/275 |
| 4,296,069 | 10/1981 | Smith et al. | 422/64 |
| 4,424,191 | 1/1984 | Jakubowicz | 422/63 |
| 4,571,087 | 2/1986 | Ranney | 422/65 |
| 4,632,808 | 12/1986 | Yamamoto et al. | 422/63 |
| 4,656,007 | 4/1987 | Douchy et al. | 422/63 |
| 4,752,449 | 6/1988 | Jackson et al. | 422/102 |
| 4,798,705 | 1/1989 | Jakubowicz et al. | 422/63 |
| 4,889,613 | 12/1989 | McNeal et al. | 422/63 |
| 4,928,540 | 5/1990 | Kido et al. | 422/63 |

Primary Examiner—David L. Lacey
Assistant Examiner—Kimberly A. Trautman
Attorney, Agent, or Firm—Dana M. Schmidt

[57] ABSTRACT

A chemical analyzer providing an analysis slide positioning apparatus and method for properly aligning a test slide relative to a sample dispenser of the chemical analyzer. The slide positioning apparatus is capable of moving the slide in three different planes of movement for effecting alignment of the slide and to control fluid application thereto. The positioning apparatus includes a platform which supports the slide, a mechanism for moving the slide on the support in a first direction, and a drive mechanism for moving the platform and the slide carried thereon in second and third directions extending perpendicular to each other and to the first direction.

21 Claims, 3 Drawing Sheets

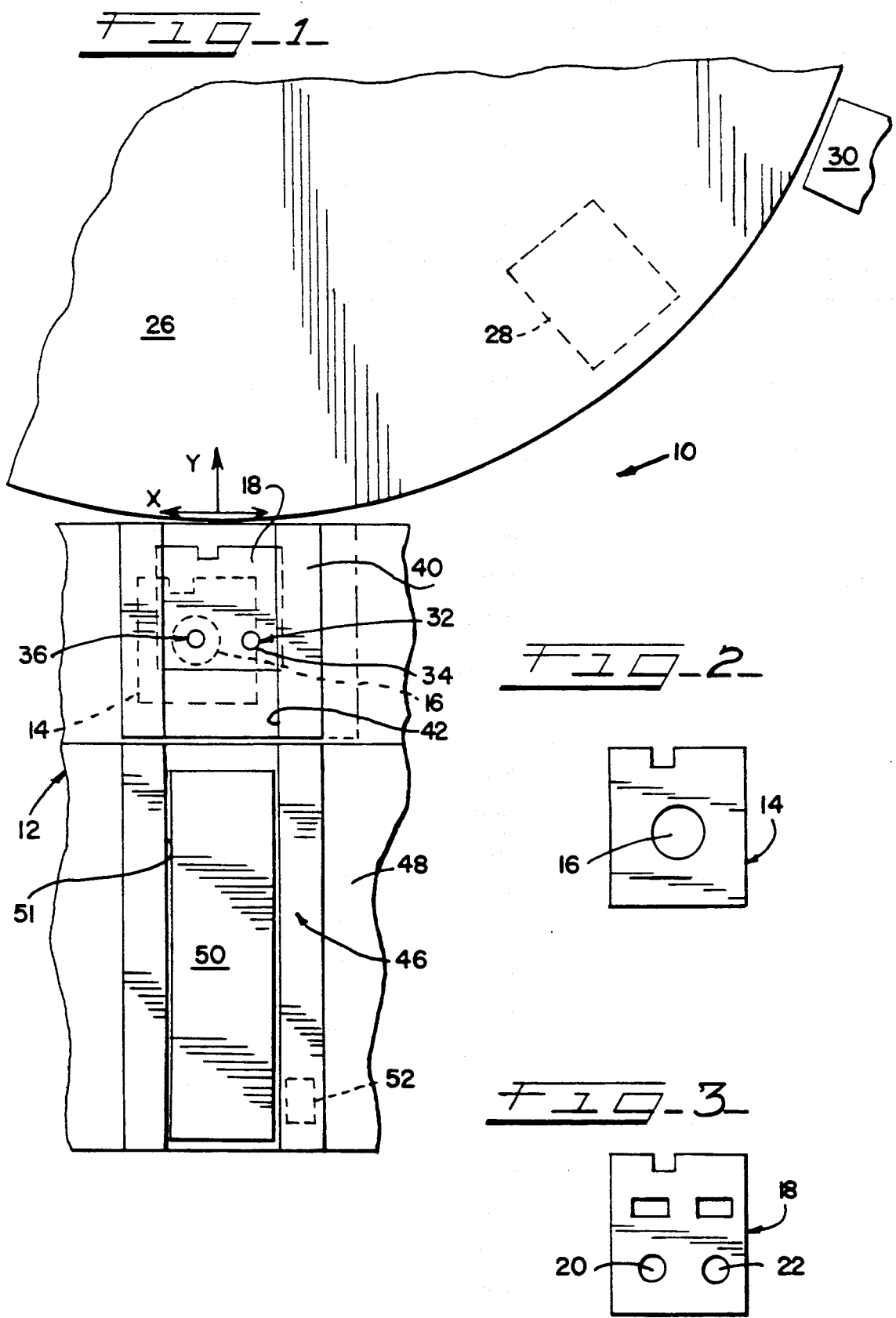

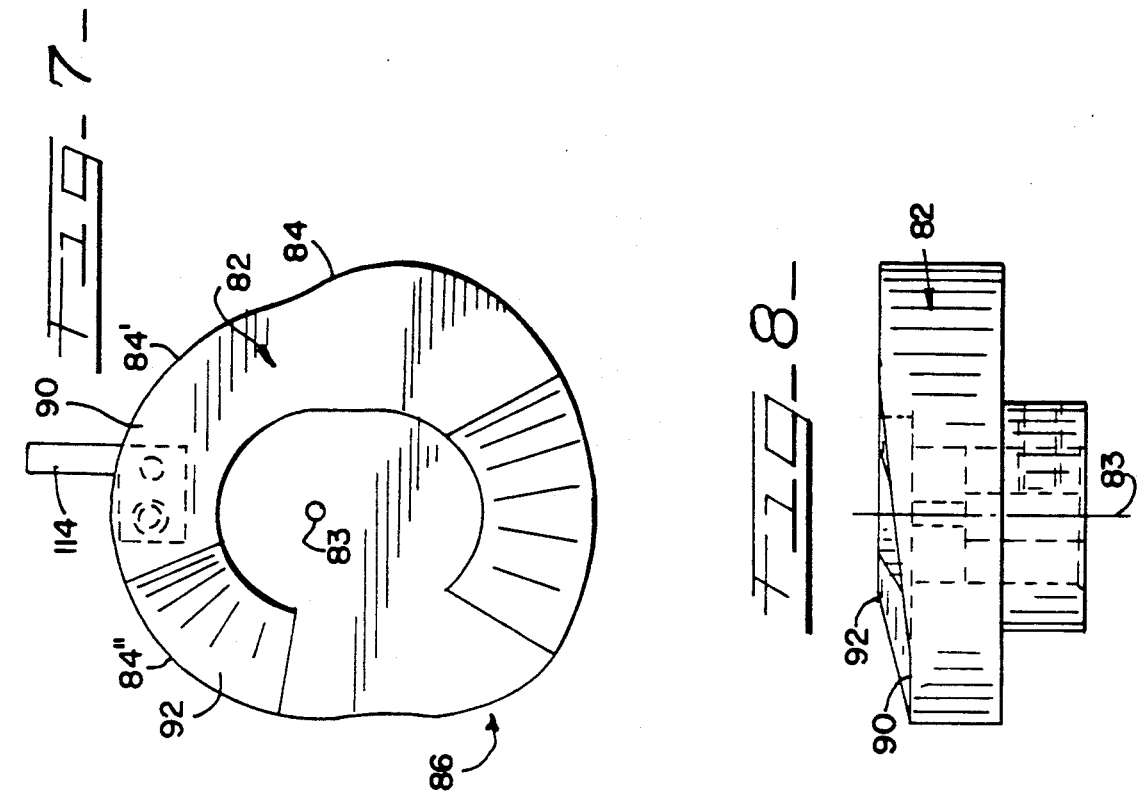
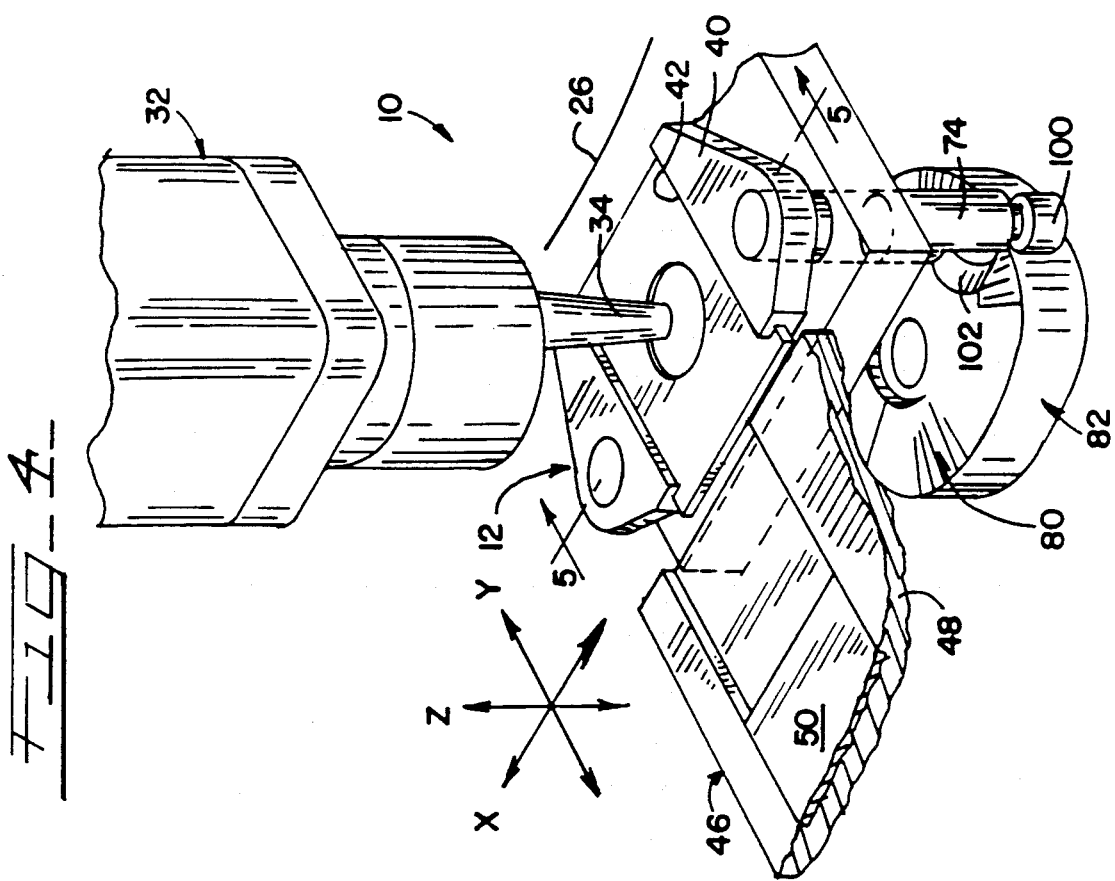

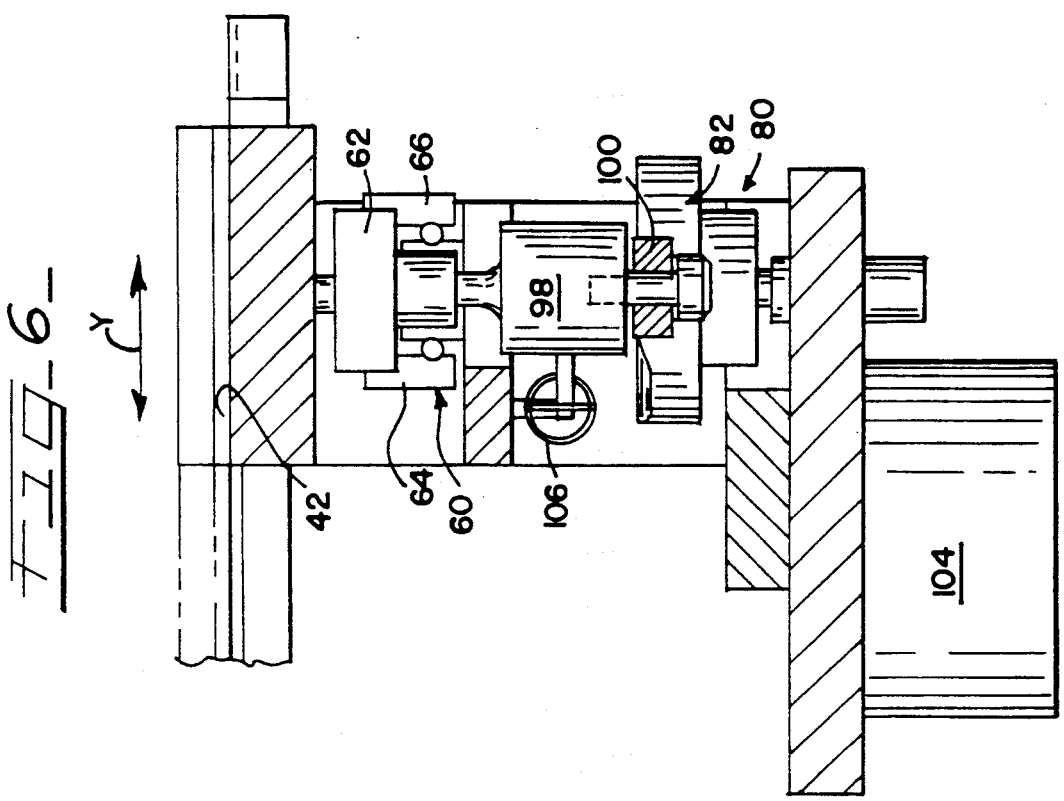
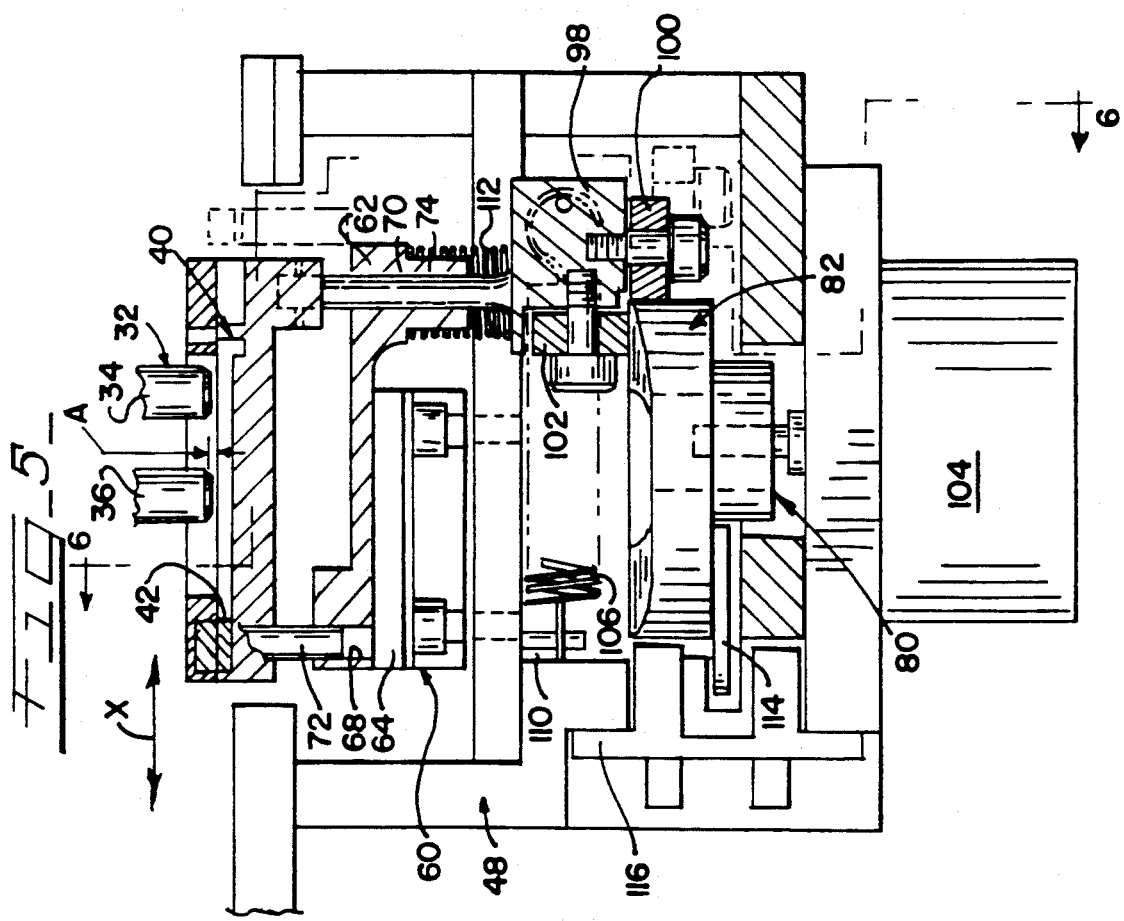

5,059,393

ANALYSIS SLIDE POSITIONING APPARATUS AND METHOD FOR A CHEMICAL ANALYZER

FIELD OF THE INVENTION

This invention generally relates to chemical apparatus for the automatic analysis of biological fluids and, more particularly, to an apparatus and method for positioning analysis test slides in a manner aiding the application of fluids to the slides.

BACKGROUND OF THE INVENTION

In recent years, a number of automated systems have been developed for carrying out quantitative chemical analyses of sample fluids. Such automated systems have proven particularly advantageous for use in clinical laboratories, especially in the analysis of blood.

For example, U.S. Pat. No. 4,296,069 discloses an apparatus which performs chemical analysis of a sample fluid deposited on an analysis test slide. A slide transfer mechanism selectively transfers an analysis test slide between an incubator and a read station. Following analysis at the read station, the test slide is either returned by the slide transfer mechanism to the incubator or is discarded by the transfer mechanism.

Different types of analysis test slides, as for example colorimetric and potentiometric slides, may be used in chemical analyzers. Although such test slides may be dimensionally similar, they have geographically different fluid deposit zones defined thereby. That is, the sample fluid applied to the test slides for analysis is applied in different locations or zones on each type of slide.

Some chemical analyzers have a sample fluid deposit device including a dual tip pipette which allows selective fluid application to both types of test slides. Because of the geographically different deposit zones on the test slides, however, the two different types of slides must be positioned differently beneath the pipettes. This is a timely and therefore, expensive procedure.

U.S. Pat. No. 4,041,995 discloses a chemical analyzer which carries test slides on a vertically movable support. This device, however, does not apply sample fluids to both colorimetric and potentiometric test slides in the same test slide holder. Moreover, there is no provision for moving the test slides in other than a vertical plane.

Presently available chemical analyzers have applied fluid to the two types of test slides in two different stations and the positioning problem has not been addressed. Moreover, certain sample fluids do not readily wick onto a test slide. Therefore, such sample fluids are not easily separated from the pipette tip and applied to the test slide by the action of the pipette alone. Other sample fluids do not readily bridge the gap between the pipette tip and the test slide and tend to wet the side of the pipette tip, hereinafter called "perfusion". Both problems are further aggravated by microgravity environments.

Analyzers used in space stations to monitor the health of astronauts have an additional constraint—the parts and test elements thereof must be kept confined lest they become floating objects that can be dangerous.

SUMMARY OF THE INVENTION

The present invention provides an improved apparatus and method for processing analysis slides in a chemical analyzer by positioning the slides in both horizontal and vertical planes. More particularly, the present invention provides a chemical analyzer having an apparatus for automatically positioning analysis test slides relative to a sample fluid deposit device. The apparatus of the present invention laterally moves a test slide in X, Y, and Z directions as hereinafter defined; which directions extend generally perpendicular to one another. As will be appreciated, the analyzer of the present invention is especially useful in microgravity environments.

In accordance with a presently preferred and illustrated embodiment, the apparatus of the present invention includes a movable platform or support for receiving and holding either a potentiometric or colorimetric analysis test slide. The platform is located adjacent to an incubator of the chemical analyzer and preferably defines a guideway which extends toward the incubator. A linearly reciprocal member aligns a test slide on the platform so that the deposit zones on the test slide are aligned relative to the sample fluid deposit device in a first direciton. The platform is moved in second and third directions extending substantially perpendicular to each other and substantially perpendicular to the first direction to further align the deposit zone on the test slide with respect to the sample fluid deposit device and to position the test slide relative to the sample fluid deposit device in a manner controlling sample fluid application to the slide. As such, there are three degrees of freedom of movement of the test slide.

The platform of the present invention includes a carrier which is guided on a stationary rail member connected to a housing member. The carrier and rail member limit movement of the platform to generally linear motion.

Precisely controlled positioning of an analysis test slide relative to the sample fluid deposit device in two opposite directions is effected by a drive mechanism including a double face cam. The cam is preferably driven by a stepper motor and includes preselected radial and height variations. Arranged in combination with the cam are cam followers which are operatively connected to the platform and impart lateral shifting and vertical movements to the platform in response to rotation of the cam. The preselected radial variations are located at different angular positions on the cam for the height variations to effect independent movement of the platform. The changing radial variations and the changing height variations on the cam are separated by regions of dwell.

Highly versatile and efficient use of the present apparatus is promoted by the manner in which the platform, with a test slide carried thereby, can be referenced relative to a "home" position whereby suitable automatic controls can thereafter operate the drive mechanism to position the test slide relative to the sample fluid deposit device. In order to reference the position of the platform, the drive mechanism includes an apparatus for sensing the angular orientation of the cam at a home position and, thereby, predict the other positions of the platform relative to that home position. By this arrangement, the position of the platform can be adjusted by selectively driving the cam in the appropriate direction.

The present invention is also directed to a method of positioning a test slide so that fluid may be dispensed to the appropriate portion of the slide. The method includes the steps of locating the slide on the platform by moving the slide in a first direction, moving the platform in a second direction perpendicular to the first direction and moving the platform in a third direction that is perpendicular to the first and second directions so that fluid may be dispensed to the appropriate location on the slide.

Providing a slide positioning apparatus having the capability of positioning an analysis test slide in any of three degrees of freedom of movement allows test slides having geographically different deposit zones to be used in chemical analyzers. Thus, an advantageous feature of the present invention is that it permits wider utilization of chemical analyzers while aiding in the application of fluids to the test slides.

While the invention is particularly suitable for use in apparatus adapted to perform analysis of blood sera in which the serum is dispensed onto a test slide, it is not limited to the analysis of blood sera as other fluids can be used with apparatus of this type.

Numerous other features and advantages of the present invention will become readily apparent from the following detailed description, the accompanying drawings, and the appended claims.

BRIEF DESCRIPTION OF THE DRAWINGS

FIG. 1 is a simplified plan view of a chemical analyzer having a slide positioning apparatus according to the present invention arranged in combination therewith;

FIG. 2 is a simplified plan view of one type of analysis test element such as a colorimetric element, which is to be used in combination with a chemical analyzer;

FIG. 3 is a simplified plan view of another type of analysis test element such as a potentiometric element, which is to be used in combination with the chemical analyzer;

FIG. 4 is a simplified perspective view of a slide positioning apparatus according to the present invention;

FIG. 5 is a partial side sectional view of the slide positioning apparatus of the present invention taken along line 5—5 of FIG. 4;

FIG. 6 is a partial front sectional view of the slide positioning apparatus of the present invention, taken generally along line 6—6 of FIG. 5;

FIG. 7 is a plan view of a drive cam element; and

FIG. 8 is a side elevational view of the cam element shown in FIG. 5.

DESCRIPTION OF THE PREFERRED EMBODIMENT

While the present invention is susceptible of embodiment in various forms, there is shown in the drawings and will hereinafter be described a presently preferred embodiment with the understanding that the present disclosure is to be considered as an exemplification of the invention, and is not intended to limit the invention to the specific embodiment illustrated.

Turning now to FIG. 1, a chemical analyzer 10 is shown as including a slide positioning apparatus 12. The chemical analyzer performs analysis of sample fluids deposited on analysis slides. The invention is adapted to operate on a variety of test slides including colorimetric and potentiometric slides.

A colorimetric test slide is schematically represented in FIG. 2 by reference number 14. Slide 14 is formed as a multi-layered substrate defining a centrally disposed deposit zone or area 16 and contains the necessary reagents for reaction with components of a biological fluid, such as blood serum, deposited thereon. Certain reactions colorimetrically produce a change in optical density in the test slide which is sensed by a reflectometer, the amount of light reflected from the element varying in accordance with the reaction and being indicative of the concentration of a particular component present in the fluid. See, e.g., U.S. Pat. No. 4,303,611.

A potentiometric test slide is schematically represented in FIG. 3 by reference number 18. Test slide 18 includes a frame having a pair of apertures 20 and 22 which define deposit areas or zones for a biological fluid and a known reference solution, such as blood serum, deposited thereon. An ion-selective electrode is positioned under each aperture. A potentiometric analysis test slide is used to potentiometrically determine the concentration of ions in a liquid test solution. See, e.g., U.S. Pat. No. 4,273,639.

It is evident from a comparison of the test slides illustrated in FIGS. 2 and 3, that they are dimensionally similar. The deposit zones or areas, however, of one test slide are located in different geographical surface areas on the substrate of one test element from the deposit zones or areas on the substrate of the other test element.

The apparatus of this invention is neither limited to use with such substrates, nor to the analysis of blood sera, as other fluids can be used with apparatus of the type disclosed. Notably, the fluid dispensed onto the test slides is deposited in very small amounts. Such predetermined drop volumes are substantially fixed and, depending on the surface area of the deposit area, range from 1 to about 30 micro liters, and preferably between about 8 and about 13 micro liters.

The kind of slide that is being supplied to the fluid dispensing station is best determined by a bar code reader (not shown) that reads bar code labels on the slides as they move towards the fluid dispensing station, as is well known in the art.

Returning to FIG. 1, the chemical anaylzer 10 further includes a conventional incubator 26 having a rotor (not shown) with a plurality of holding stations that receive and hold spotted test slides. Analysis means are located adjacent the incubator. As illustrated, a colorimetric read station 28 carrying a conventional reflectometer is located to one side of and below the incubator 26. A potentiometric station 30 is also disposed adjacent to the incubator in a circumferentially spaced relationship to read station 28. Incubator 26 and analysis stations 28 and 30 are substantially conventional devices which, although used in combination with the present invention, are not essential elements thereof.

As illustrated in FIGS. 1 and 4, a fluid sample dispenser or pipette 32, defining a fluid sample deposit station or zone, is located adjacent to the incubator 26. In a preferred form of the invention, the fluid sample dispenser or pipette 32 includes a pair of laterally spaced pipette tips 34 and 36 as shown in FIG. 5. It should be appreciated, however, that the present invention is equally applicable to a fluid sample dispenser having a single pipette tip. The fluid sample dispenser or pipette 32 is an apparatus which dispenses fluid in any repetitive dispensing operation. When discussed in terms of that which is dispensed, unless otherwise stated "fluid" is used to mean a fluid capable of forming pendant drops.

The slide positioning apparatus 12 of the present invention is configured such that a test slide is positioned relative to the sample fluid deposit station by movement of the test slide along three axes. Accordingly, and for clarity of the present disclosure, reference will be made in FIG. 4 to a horizontal Y-axis which extends in a direction toward and away from incubator 26, a horizontal X-axis extending perpendicular to the Y-axis, and a vertical Z-axis extending perpendicularly to the X-axis and the Y-axis.

Particularly as illustrated in FIG. 4, the slide positioning apparatus 12 includes a movable platform or support 40 which receives and positions either a colorimetric or potentiometric analysis test slide relative to the sample fluid deposit station 32. The platform 40 may be shaped to receive and hold a test slide in proper alignment as by the provision of a recessed guideway 42 in which the test slide is positioned.

In the illustrated embodiment, a suitable transfer mechanism 46 automatically positions a test slide in the guideway 42 of the platform 40. As illustrated in FIG. 4, mechanism 46 moves a test slide relative to the sample fluid deposit station 32 in a Y direction extending parallel to the longitudinal axis of the guideway 42. A drive mechanism 80 positions the platform 40 and the test slide carried thereby in both X and Z directions relative to the fluid sample deposit station 32.

In its preferred form, the transfer mechanism 46 includes a stationary housing 48 located adjacent incubator 26 and a linearly reciprocal blade member 50 which is adapted to engage one end of a slide in a guideway 51 so as to linearly move the slide toward the incubator 26 and relative to the fluid deposit station 32. As illustrated in FIG. 1, transfer mechanism 46 further includes suitable sensors 52 for monitoring the extent of linear extension of member 50. Any sensor may be used. For example, mechanical flags can trigger limit switches, the flags being mounted on blade member 50. Alternatively, a photo optical or magnetic reader can optionally detect an appropriate marker on blade member 50. A preferred method features the location of sensor 52 under blade member 50, to sense a flag mounted on a drive belt (not shown) for blade member 50, and counting the steps of the stepper motor that drives the belt and blade member 50 from the "home" position of the flag.

Platform 40 of the slide positioning mechanism 12 is supported for independent movement in two opposite straightline directions. As illustrated in FIGS. 5 and 6, a carrier assembly 60 provides controlled movement of platform 40 in the X-axis direction. Carrier assembly 60 preferably includes an elongated carrier 62 that reciprocally slides between and along one or preferably a pair of stationary, preferably linear, rails 64 and 66. Rails 64 and 66 are suitably affixed to an extension of housing 48 as shown in FIG. 5 and FIG. 6. Although rails 64 and 66 permit sidewise movement of carrier 62 relative to the stationary housing 48, they also serve to prevent vertical displacement of carrier 62 relative to housing 48.

Opposite ends of carrier 62 define vertically extending apertures 68 and 70. One end of an upstruck post 72 is fixed in aperture 68. The opposite end of post 72 supports one side of platform 40. An elongated upstruck post 74 freely passes through aperture 70 defined by carrier 62. The upper end of post 74 is connected to and supports the opposite side of platform 40.

The other end of post 74 is spring loaded against the driven cam 82 which imparts independent lateral shifting and vertical movements to platform 40.

Rotatably driven cam 82 is an essential element of drive mechanism 80. As best illustrated in FIGS. 7 and 8, cam 82 is a double face element having an axis of rotation 83, a plurality of preselected radial face variations 84 and 86 and a plurality of preselected height face variations 90 and 92. As used herein "radial face" refers to surfaces having a varying radial distance from axis 83. "Height face" variations refer to distance variations measured along, or parallel to axis 83. As will be appreciated, the number of face variations on the cam may vary depending on the number of locations desired for platform 40. The radial face variations are located on the cam at different angular positions from the height face variations such that the shifting and lifting movements imparted by cam 82 are independent of each other. All of the changing portions on the cam are separated by regions of dwell. Thus, for example, radial face portion 84', FIG. 7, is equidistant from axis 83 as is radial face portion 84", but the height face portions (92 at 84"and 90 at 84') vary in those two locations. This provides vertical motion to platform 40 without motion in the X direction. Similarly, constant height face portions are provided for varying radial face portions, to provide movement in the Z direction only.

Returning to FIGS. 5 and 6, in its presently preferred form, the lower end of pin 74 terminates in a mounting block 98. A first cam follower 100, which rides on the radial cam edge of cam 82, is rotatably connected through suitable means to mounting block 98. A second cam follower 102, which rides on a vertical top cam face of cam 82 is also rotatably connected through suitable means to block 98. A stepper motor 104 carried by stationary housing 48 imparts rotational movement to the cam 82.

A resilient member 106 maintains roller 100 in continual contact with the radial face of cam 82. In its preferred form, resilient member 106 is a tension spring, one end of which is connected to mounting block 98 and the opposite end of which is connected to a pin 110 depending from the housing 48. Another resilient member 112 imparts a vertical force sufficient to maintain roller 102 in continual contact with the vertical top cam face of cam 82. As illustrated, resilient member 112 is in the form of a compression spring which is captively arranged about pin 74 between carrier 62 and the top of mounting block 98. Because carrier 62 is prevented from vertical displacement, spring 48 acts to continually urge cam follower 102 against the top face of radial cam 82. Pin 74 is thus free to rise and fall within aperture 70.

Efficient operation of the present apparatus is promoted by the manner in which platform 40 can be referenced relative to a "home" position such that a slide element carried thereby may be properly positioned relative to the fluid sample deposit zone 32. To this end, a flag 114 (FIGS. 5 and 7) in the form of a flat projection radially extends from one side of cam 82 and cooperates with an optical sensor 116 (FIG. 5) carried by housing 48. The position of cam 82, and thereby the position of platform 40, is determined by the number of steps that the stepper motor is moved from a "home" position. Other known means may also be used for accurately positioning the platform.

In operation, a test slide is presented to the fluid sampling deposit station 32 by the slide positioning mechanism 12 of the present invention. In FIG. 1, a potentiometric test element 18 is shown in solid lines. Pusher slide 50 moves test element 18 along the guideway 42 in the Y-axis direction until the deposit zones 20 and 22 of the test slide are substantially aligned with the position for pipette tips 34 and 36 (shown as circles in FIG. 1). Sensor 52 controls the linear distention of pusher slide 50 to properly align test element 18 beneath the fluid sample deposit station 32, as shown.

Suitable software controls the motor 104 to rotatably drive the cam 82 in a manner shifting and lifting the platform 40 such that the test slide carried thereon is moved into position relative to the fluid sample deposit station 32. Shifting and lifting movements of the cam are independent of each other. Any given test slide can be shifted only, lifted only, or both shifted and lifted as determined by the software controlling motor 82. Such software is conventional and can be used with any conventional microprocessor, not shown.

As will be appreciated, the position of platform 40 is determined by the step counts from a "home" position. Notably, all regions of transition on cam 82 are preferably separated by regions of dwell. Fluid deposits to the test slide and other operations are performed with the cam 82 at dwell to eliminate platform position errors caused by slight cam position errors. That is, the dwell regions on the cam make the cam positions non-critical. As such, wide tolerances are permitted in manufacturing and placement of the sensors for monitoring the positions of the cam.

For a potentiometric slide 18, platform 40 need be shifted substantially no distance in the X direction as shown in FIG. 1 because of the preferred use of a dual pipette.

When a colorimetric test slide is to be presented to the fluid sampling deposit station 32, platform 40 is shifted so that the deposit zone 16 on the colorimetric test element (shown in phantom lines in FIG. 1) will be aligned with pipette 36. As such, the same fluid sample deposit device can be used to meter a fluid sample onto either a colorimetric slide or a potentiometric slide. As will be appreciated, the positioning of a colorimetric slide by the slide positioning mechanism 12 is effected in substantially the same manner as that described above with respect to the potentiometric slide element, except that the X and Y positions are different.

By bringing either slide into close proximity to the pipette and then slowly moving it away during or after fluid deposit, the fluids being deposited are easily separated from the pipette tip. Moreover, the present invention properly positions either type of test slide relative to a fluid sample deposit device in a manner that minimizes perfusion. The preferred separation distance and relative movement suited for each chemistry is already a function of current practices in the industry, so that no further detail need be recited. Because each assay may prefer a different set of separation and movement parameters, the present invention is ideally suited to accommodate those by controlling the motion of platform 40 in the Z direction.

For purposes of illustration, separation distance "A", FIG. 5, preferably is about .635 mm in the case of a slide used to assay Glucose, and for a slide for assaying Sodium, "A" is also preferable about .635 mm.

Since the control of the spacing in the Z direction acts to minimize perfusion, the present invention is especially useful in microgravity environments where the absence of gravity tends to aggravate perfusion problems.

The invention has been described in detail with particular reference to certain preferred embodiments thereof, but it will be understood that variations and modifications can be effected within the spirit and scope of the invention.

What is claimed is:

1. A chemical analyzer including an incubator, at least one read station disposed adjacent to one side of the incubator, a sample fluid dispenser station which is constructed so as to provide the formation of pendant fluid drops, and an apparatus for aligning and vertically positioning test slides having geographically different fluid deposit zones relative to the sample fluid dispenser station to control fluid application to said slides, said apparatus comprising:

a movable platform defining a guideway leading to said incubator, said guideway defining a support for a slide beneath said sample fluid dispenser station to allow a pendant fluid drop to be deposited upon a fluid deposit zone of said slide;

linearly reciprocal means for moving said slide in a linear direction in said guideway toward said incubator and in a manner positioning said slide relative to said sample fluid dispenser station so as to dispense fluid thereon; and cam driven means for moving said platform and the slide carried thereby in only two directions extending generally perpendicular to each other and to the linear direction of said slide relative to said sample fluid dispenser station in a manner controlling fluid application to said slide.

2. The chemical analyzer of claim 1 wherein said movable platform is supported for linear movement on a rail connected to a stationary housing.

3. The chemical analyzer of claim 1 wherein said cam driven means includes a rotatably driven cam having preselected radial variations and preselected height variations.

4. The chemical analyzer of claim 3 wherein the radial variations are located on said cam at different angular positions from said height variations such that the shifting and lifing movements imparted by said cam are independent of each other.

5. The chemical analyzer of claim 1 further including means for sensing movement of said platform relative to a "home" position.

6. The chemical analyzer of claim 1 wherein said cam driven means includes a rotatably driven cam having changing radial portions and changing height portions, the changing portions on said cam being separated by regions of dwell.

7. A method of depositing fluid from fluid dispensing means onto a test slide which comprises (a) locating the slide on a platform by moving said slide in a first direction onto said platform;

(b) moving the platform in only two directions one of which is perpendicular to said first direction;

and the other of which is perpendicular to said first and second directions to locate the slide under the fluid dispensing means; and (c) dispensing fluid onto the slide.

8. A method as in claim 7 which includes the step of determining the type of slide being positioned to control the amount of movement in each direction.

9. A method as in claim 7 wherein the test slide is a colorimetric slide.

10. A method as in claim 7 wherein the test slide is a potentiometric slide.

11. A method as defined in claim 8, wherein said step a) comprises moving the slide a greater distance in said first direction if the slide is a potentiometric slide, compared to the distance moved if it is a colorimetric slide.

12. In slide positioning apparatus for automatically positioning analysis slides in an analyzer relative to a sample dispenser to control the application of sample fluid to said slides, the slide positioning apparatus comprising a movable platform for supporting an analysis slide thereon, and slide transfer means for positioning a slide on said platform relative to the sample dispenser in a first direction;

the improvement wherein said apparatus includes a carrier assembly mounted for moving said platform in only two other directions, extending generally perpendicular to said first direction and generally perpendicular to one another, to position said slide carried by said platform relative to said sample dispenser, and means controlling said slide transfer means to alter slide positioning in said first direction.

13. Apparatus according to claim 12, wherein said carrier assembly is mounted on at least one linear rail which limits movement of said platform to movement substantially in a straight line.

14. Apparatus according to claim 12 or 13, wherein said carrier assembly includes a double faced motor driven cam.

15. Apparatus according to claim 14, wherein said carrier assembly includes a first cam follower which rides on a radial cam surface of said cam, and a second cam follower which rides on another cam surface of said cam.

16. Apparatus according to claim 15, wherein said cam has preselected face variations in radius and height, these variations being operable to move said platform in said other directions respectively relative to said sample dispenser.

17. Apparatus according to claim 16, wherein said preselected radius face variations are located at different angular positions on said cam from said height face variations to effect independent movement of said platform in said other directions.

18. Apparatus according to claim 17, wherein said preselected radius face variations are separated by regions of dwell.

19. Apparatus according to claim 12, wherein said carrier assembly includes means for monitoring the position of said platform relative to a "home" position.

20. Apparatus according to claim 19, wherein said cam is driven by a stepper motor, and said position of said platform from said "home" position is monitored by a step count of said motor.

21. Apparatus according to claim 12 or 13, wherein said slide transfer means includes a linearly reciprocating blade member which engages a slide and positions it on said platform as a function of the linear displacement of said blade member.

* * * * *